United States Patent [19]

Park et al.

[11] Patent Number: 5,138,082

[45] Date of Patent: Aug. 11, 1992

[54] PROCESS FOR PREPARATION OF ORGANOSILICON HALIDES

[75] Inventors: Won S. Park; William R. Beard, both of Baton Rouge, La.

[73] Assignee: Ethyl Corporation, Richmond, Va.

[21] Appl. No.: 809,429

[22] Filed: Dec. 18, 1991

[51] Int. Cl.$^5$ ................................................. C07F 7/08
[52] U.S. Cl. ..................................................... 556/478
[58] Field of Search .......................................... 556/478

[56] References Cited

U.S. PATENT DOCUMENTS

| | | | |
|---|---|---|---|
| 2,762,824 | 9/1956 | Brown | 556/478 |
| 3,927,059 | 12/1975 | Sibley et al. | 556/478 |
| 4,711,966 | 12/1987 | Nelson | 556/478 |
| 4,916,245 | 4/1990 | Nelson | 556/478 |
| 4,999,447 | 3/1991 | Nelson | 556/478 |

Primary Examiner—Paul F. Shaver
Attorney, Agent, or Firm—Richard J. Hammond

[57] ABSTRACT

A process for preparing a silane mixture of the formula $$SiR_nX_{4-n}$$

where R is $C_1$ to $C_{12}$ linear or branched alkyl, phenyl or phenyl substituted with one or more $C_1$ to $C_6$ linear or branched alkyl; X is chloro, bromo or iodo; and n is an integer from 1 to 4; comprising reacting silicon tetrafluoride with $(R)_3Al_2X_3$, where R and X are as previously described, at a temperature of about 325° C. to about 360° C.

10 Claims, No Drawings

PROCESS FOR PREPARATION OF ORGANOSILICON HALIDES

This invention relates to the manufacture of silicon compounds and more particularly to a new process for making organosilicon halides.

Organosilicon halides, as for example, methylsilicon chlorides ($MeSiCl_3$, $Me_2SiCl_2$, $Me_3SiCl$), are manufactured commercially by reacting methylchloride with elemental silicon or by reacting Grignard reagents with silicon halide compounds. These processes have several disadvantages particularly with regard to the economics of the use of catalysts and reagents.

U.S. Pat. No. 2,762,824 discloses the manufacture of organosilicon halides such as the alkyl and aryl silicon halides directly from the corresponding alkyl- and arylaluminum halides by reaction with silicon tetrafluoride. These alkyl- and arylaluminum halides can be prepared by means from alkyl or aryl halides and aluminum metal.

The reaction disadvantageously proceeds in two steps and requires the isolation of an intermediate mixture of alkyl or aryl aluminum halides which are in turn further reacted with silicon tetrafluoride at significantly higher temperatures. The final product is an essentially equal mixture of $(CH_3)_3SiCl$, $(CH_3)_2SiCl_2$, and $CH_3SiCl_3$ when methyl chloride is employed.

It is accordingly an object of this invention to provide an improved process for the manufacture of organosilicon halides with higher dialkylsilicon dihalide content. Other objects and advantages of this invention will become apparent as the description proceeds.

A wide variety of organosilicon halides of the formula $SiR_nX_{4-n}$ (where n is from 1 to 4) can be manufactured according to this invention. Thus, R is $C_1$ to $C_6$ linear or branched alkyl, phenyl, or phenyl substituted with one or more $C_1$ to $C_6$ linear or branched alkyl, $C_1$ to $C_6$ linear or branched alkoxy, halo, cyano, carboxylic acid, $C_1$ to $C_6$ linear or branched alkyl ester of said carboxylic acid or nitro. Preferably, R is methyl, ethyl, n-propyl or i-propyl, phenyl, para-phenyl substituted at positions 2, 3 or 4 with at least one methyl, ethyl, n-propyl, 1-propyl, n-butyl, sec-butyl or t-butyl group, or at least one methoxy or ethoxy group or at least one halo (chloro, bromo or fluoro) group, or with carboxylic acid or methyl or ester carboxylic ester thereof. Most preferably, R is methyl, ethyl or phenyl. Especially preferred is methyl when n is 2.

Normally, the halides which are most useful in this invention are confined to the chlorides, bromides and iodides. Although slight reaction is obtained with some fluorides, they are of generally less importance. Preferably, the halide is chloro, especially when R is $C_1$ to $C_6$ linear or branched alkyl.

Typical examples of alkyl and aryl halides suitable for the reaction of this invention are methyl chloride, ethyl chloride, isopropyl chloride, n-propyl chloride, ethyl bromide, methyl bromide, methyl iodide, ethyl iodide, n-propyl iodide, isopropyl iodide, hexyl iodide, heptyl iodide, octyl iodide, p-tolyl iodide and phenyl iodide.

Each of the above alkyl and aryl halides results in corresponding alkyl or aryl silicon halides. For example, when methyl chloride is employed, the final product is $(CH_3)_2SiCl_2$ mixed with $(CH_3)_3SiCl$, $CH_3SiCl_3$ and other methylsilicon compounds. Likewise, when ethyl chloride or methyl bromide is employed, the final products are $(C_2H_5)_2SiCl_2$ and $(CH_3)_2SiBr_2$, respectively.

Other typical examples of organosilicon halides which can be made by this invention are as follows: diphenyl silicon iodide, phenyl silicon iodide, naphthyl silicon bromide, naphthyl silicon iodide and benzyl silicon chloride.

The reaction is preferably carried out in the presence of a Lewis acid catalyst, such as aluminum chloride, aluminum fluoride, copper (I) nitrile, or iodine. In general, it is desired to use between about 0.05–0.2% of catalyst based upon the weight of the aluminum. A more preferred range of catalyst is 0.075–0.15%. Higher concentrations can be used, but such concentrations do not materially increase the reaction rate and also tend to contaminate the product. In some cases, lower concentrations can be employed.

The reaction is generally carried out at a pressure of between about 1 and 20 atmospheres. Normally, it is preferred to maintain the pressure between about 1 and 5 atmospheres. The temperature of reaction should be maintained above 325° C. and up to about 375° C. Below the former temperature, the reaction rate is materially reduced. A preferred temperature of operation is between 340°–360° C. This reaction is normally carried out in the absence of any solvent, since in many instances the catalyst tends to form a complex with the solvent.

A wide variety of concentrations of reactants can be employed in this reaction. However, stoichiometric quantities are generally preferred.

The reaction can be carried out in a wide variety of reaction vessels. A glass-lined stirred autoclave is ordinarily preferred. However, in a continuous operation, a tube type reactor can be employed.

The following examples are working examples and are for illustrative purposes only.

All reactions and handling of air-sensitive materials were conducted in a nitrogen atmosphere; GC/MS analyses were performed using a Finnegan 4500 Gas Chromatograph/Mass Spectrometer. Products were identified by comparing analytical results with those of authentic commercial samples. MASC is methylaluminum sesquichloride.

TABLE

| | | | | REACTIONS OF $SiF_4$ WITH MASC[a] | | | | |
|---|---|---|---|---|---|---|---|---|
| | | TEMP, | PMAX, | | PRODUCTS, %[b] | $Me_3SiCl-$ | | |
| EXAMPLE | TIME, h | °C. | psi | ADDITIVE | $SiMe_4$ | $SiCl_4$ | $MeSiCl_3$ | $Me_2SiCl_2$ | OTHERS[c] |
| 1 | 3 | 150–220 | 150 | — | 19 | 46 | 17 | 0 | 18 |
| 2 | 16 | 200–220 | 200 | — | 31 | 55 | 6 | 0 | 8 |
| 3 | 16 | 200–220 | 200 | 10 mole % $AlCl_3$ | ~0 | 76 | ~0 | 19 | 5 |
| 4 | 16 | 170–180 | 200 | 10 mole % $AlCl_3$ + 16 mole % $MeSiHCl_2$ | ~0 | 62 | 2 | 18 | 18 |
| 5[d] | 16 | 260–300 | 90 | 10 wt % $AlCl_3$ + 18 wt % $MeSiHCl_2$ | ~0 | 8 | ~0 | 86 | 6 |

TABLE-continued

REACTIONS OF SiF$_4$ WITH MASC[a]

| EXAMPLE | TIME, h | TEMP, °C. | PMAX, psi | ADDITIVE | PRODUCTS, %[b] SiMe$_4$ | Me$_3$SiCl— SiCl$_4$ | MeSiCl$_3$ | Me$_2$SiCl$_2$ | OTHERS[c] |
|---|---|---|---|---|---|---|---|---|---|
| 6 | 3 | 350 | 250 | — | ~0 | 6 | 10 | 70 | 14 |

[a]MASC 16.7 mmole, SiF$_4$ 25 mmole, in a 45 ml SS bomb autoclave.
[b]Product distribution of liquid products were analyzed by GC/MS with approximately ±3% error.
[c]Remainders are other methylated or nonmethylated chlorofluorosilanes.
[d]Redistribution reaction using combined liquid product mixture of Examples 1 and 2. A total of 68 wt % of starting material was isolated as liquid products.

We claim:

1. In a process for preparing a silane mixture of the formula

Si R$_n$ X$_{4-n}$ where R is C$_1$ to C$_{12}$ linear or branched alkyl, phenyl or phenyl substituted with one or more C$_1$ to C$_6$ linear or branched alkyl, C$_1$ to C$_6$ linear or branched alkoxy, halo, cyano, carboxylic acid, C$_1$ to C$_6$ linear or branched alkyl ester of carboxylic acid or nitro; X is chloro, bromo or iodo; and n is an integer from 1 to 4; by reacting silicon tetrafluoride with (R)$_3$Al$_2$X$_3$, where R and X are as previously described, the improvement comprising carrying out the reaction at a temperature of about 325° C. to about 375° C.

2. The process according to claim 1 wherein said temperature is from about 340° C. to about 360° C.

3. The process according to claim 2 wherein R is C$_1$ to C$_6$ linear or branched alkyl and X is chloro.

4. The process according to claim 3 wherein R is methyl.

5. The process according to claim 4 wherein n is 2.

6. The process according to claim 5 wherein a catalytically effective amount of a Lewis acid is added to the reaction.

7. The process according to claim 6 wherein said Lewis acid is aluminum chloride, aluminum fluoride, or copper (I) nitrile.

8. The process according to claim 7 wherein R is C$_1$ to C$_6$ linear or branched alkyl and X is chloro.

9. The process according to claim 8 wherein R is methyl.

10. The process according to claim 9 wherein n is 2.

* * * * *